United States Patent [19]

Goldmann et al.

[11] Patent Number: 4,801,715
[45] Date of Patent: Jan. 31, 1989

[54] CERTAIN 4-THIENYL-DIHYDROPYRIDINES

[75] Inventors: Siegfried Goldmann; Hilmar Bischoff; Walter Puls; Joachim Bender, all of Wuppertal; Dieter Petzinna, Wesel; Klaus Schlossmann, Wuppertal, all of Fed. Rep. of Germany

[73] Assignee: Bayer Aktiengesellschaft, Leverkusen, Fed. Rep. of Germany

[21] Appl. No.: 937,870

[22] Filed: Dec. 4, 1986

[30] Foreign Application Priority Data

Dec. 18, 1985 [DE] Fed. Rep. of Germany ....... 3544693

[51] Int. Cl.$^4$ ......................................... C07D 491/048
[52] U.S. Cl. ........................................ 546/116; 544/58.6; 544/127; 544/362
[58] Field of Search ............... 546/116; 544/58.6, 127, 544/362; 514/222, 231, 253, 302

[56] References Cited

U.S. PATENT DOCUMENTS 4,145,432  3/1979  Sato ..................................... 546/113
4,532,248  7/1985  Franckowiak et al. ............. 514/352
4,647,568  3/1987  Görlitzer et al. .................... 546/116

FOREIGN PATENT DOCUMENTS 0111453  6/1984  European Pat. Off. .
0111455  6/1984  European Pat. Off. .
2629892  1/1977  Fed. Rep. of Germany .

Primary Examiner—Alan L. Rotman
Assistant Examiner—Bernard I. Dentz
Attorney, Agent, or Firm—Sprung Horn Kramer & Woods

[57] ABSTRACT

Blood sugar levels are reduced by administration of novel 4-thienyl-dihydropyridines of the formula

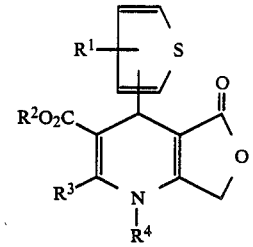

in which
  $R^1$ represents 1 or 2 halogen atoms, or represents straight-chain, branched or cyclic alkyl with up to 8 carbon atoms,
  $R^2$ represents a straight-chain, branched or cyclic, saturated or unsaturated hydrocarbon radical which has up to 15 carbon atoms, is optionally interrupted by one or two oxygen atoms, -N-phenyl or —SO$_n$—(n=0, 1 or 2) and is optionally substituted by halogen, phenyl, hydroxyl, cyano, amino, $C_1$–$C_6$-alkylamino, di-$C_1$–$C_6$-alkylamino, pyridyl, piperidino, N-phenylpiperazino, N-methylpiperazino, morpholino or N-benzyl-N-benzyl-N-methyl-amino,
  $R^3$ represents hydrogen, or represents straight-chain, branched or cyclic alkyl which has up to 6 carbon atoms and is optionally substituted by halogen, hydroxyl, amino or amino-$C_1$–$C_6$-alkoxy, or represents cyano or formyl and
  $R^4$ represents hydrogen or a straight-chain, branched or cyclic alkyl radical which has up to 10 carbon atoms, is optionally interrupted by one or two oxygen atoms in the chain and is optionally substituted by halogen, cyano, hydroxyl, phenyl, carboxyl, $C_1$–$C_6$-alkoxycarbonyl, amino, $C_1$–$C_6$-alkylamino, di-$C_1$–$C_6$-alkylamino, formyl, piperidino, morpholino or thiomorpholino,
or physiologically acceptable salts thereof.

4 Claims, No Drawings

CERTAIN 4-THIENYL-DIHYDROPYRIDINES

The invention relates to 4-thienyl-dihydropyridine-lactones, processes for their preparation and their use in medicaments, in particular in medicaments which influence the blood sugar.

The present invention relates to 4-thienyl-dihydropyridines of the general formula (I)

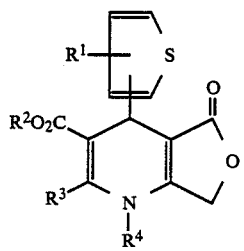

in which
- $R^1$ represents 1 or 2 halogen atoms, or represents straight-chain, branched or cyclic alkyl with up to 8 carbon atoms,
- $R^2$ represents a straight-chain, branched or cyclic, saturated or unsaturated hydrocarbon radical which has up to 15 carbon atoms, is optionally interrupted by one or two oxygen atoms, -N-phenyl or $-SO_n-$ (n=0, 1 or 2) and is optionally substituted by halogen, phenyl, hydroxyl, cyano, amino, $C_1-C_6$-alkylamino, di-$C_1-C_6$alkylamino, pyridyl, piperidino, N-phenylpiperazino, N-methylpiperazino, morpholino or N-benzyl-N-methyl-amino,
- $R^3$ represents hydrogen, or represents straight-chain, branched or cyclic alkyl which has up to 6 carbon atoms and is optionally substituted by halogen, hydroxyl, amino or amino-$C_1-C_6$-alkoxy, or represents cyano or formyl and
- $R^4$ represents hydrogen or a straight-chain, branched or cyclic alkyl radical which has up to 10 carbon atoms, is optionally interrupted by one or two oxygen atoms in the chain and is optionally substituted by halogen, cyano, hydroxyl, phenyl, carboxyl, $C_1-C_6$-alkoxycarbonyl, amino, $C_1-C_6$-alkylamino, di-$C_1-C_6$alkylamino, formyl, piperidino, morpholino or thiomorpholino, in the form of their isomers, isomer mixtures, racemates and optical antipodes and their physiologically acceptable salts.

Compounds of the formula (I) which are of particular interest are those in which
- $R^1$ represents 1 or 2 fluorine, chlorine or bromine atoms, or represents straight-chain or branched alkyl with up to 6 carbon atoms,
- $R^2$ represents a straight-chain, branched or cyclic saturated or unsaturated hydrocarbon radical which has up to 10 carbon atoms, is optionally interrupted by one or two oxygen atoms or by N-phenyl and is optionally substituted by one or more fluorine, chlorine, bromine, phenyl, hydroxyl, cyano, amino, $C_1-C_4$-alkylamino, di-$C_1-C_4$-alkylamino, N-phenylpiperazino or N-benzyl-N-methylamino groups,
- $R^3$ represents cyano, or represents straight-chain or branched alkyl which has up to 4 carbon atoms and is optionally substituted by fluorine, chlorine, bromine, hydroxyl or amino-$C_1-C_4$-alkoxy and
- $R^4$ represents hydrogen or a straight-chain, branched or cyclic alkyl radical which has up to 8 carbon atoms, is optionally interrupted by one or two oxygen atoms in the chain and is optionally substituted by one or more fluorine, chlorine, bromine, cyano, phenyl, carboxyl, $C_1-C_4$-alkoxycarbonyl, amino, $C_1-C_4$-alkylamino, di-$C_1-C_4$-alkylamino or morpholino groups, in the form of their isomer mixtures, racemates and optical antipodes, and their physiologically acceptable salts.

Compounds of the formula (I) which are of very particular interest are those in which
- $R^1$ represents fluorine or chlorine, or represents straight-chain or branched alkyl with up to 4 carbon atoms,
- $R^2$ represents a straight-chain, branched or cyclic hydrocarbon radical which has up to 8 carbon atoms, is optionally interrupted by an oxygen atom and is optionally substituted by one or more fluorine, chlorine, phenyl, hydroxyl, cyano, amino, $C_1-C_3$-alkylamino, di-$C_1-C_3$-alkylamino or N-benzyl-N-methyl-amino groups,
- $R^3$ represents $C_1-C_4$alkyl which is optionally substituted by hydroxyl and
- $R^4$ represents hydrogen, or represents a straight-chain, branched or cyclic alkyl radical with up to 6 carbon atoms, in the form of their isomers, isomer mixtures, racemates and optical antipodes, and their physiologically acceptable salts.

Compounds of the formula (I) which may be mentioned in particular are those in which
- $R^1$ represents chlorine or $C_1-C_4$-alkyl, $R^2$ represents a straight-chain or branched alkyl radical with up to 6 carbon atoms,
- $R^3$ represents $C_1-C_4$-alkyl and $R^4$ represents hydrogen or an alkyl radical with up to 4 carbon atoms, in the form of their isomers, isomer mixtures, racemates and optical antipodes and their physiologically acceptable salts.

The substances according to the invention can exist in the form of their salts. These are in general salts of the substances according to the invention with inorganic or organic acids. However, the physiologically acceptable salts of the substances according to the invention with inorganic or organic acids are preferred. Examples which may be mentioned are: hydrohalides, bisulphates, sulphates, hydrogen phosphates, acetates, maleates, citrates, fumarates, tartrates, lactates or benzoates.

The compounds according to the invention exist in stereoisomeric forms which either behave as mirror images (enantiomers) or do not behave as mirror images (diastereomers). The invention relates both to the antipodes and to the racemic forms as well as diastereomer mixtures. The racemic forms, like the diastereomers, can be resolved into the stereoisomerically pure constituents in a known manner (compare E. L. Eliel, Stereochemistry of Carbon Compounds, McGraw Hill, 1962).

The compounds of the general formula (I) according to the invention can be prepared by a process in which [A]aldehydes of the general formula II

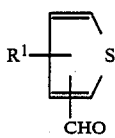 (II)

in which
R$^1$ has the meaning given, are reacted with acetoacetic acid esters of the general formula III

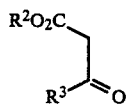 (III)

in which
R$^2$ and R$^3$ have the abovementioned meaning, and with enamines of the general formula IV

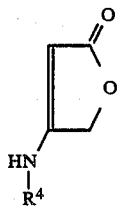 (IV)

in which
R$^4$ has the meaning given, in inert solvents, or by a process in which
[B]ylidene compounds of the general formula V

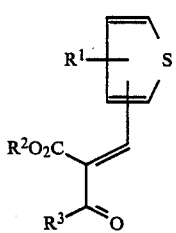 (V)

in which
R$^1$, R$^2$ and R$^3$ have the meaning given, are reacted with enamines of the formula IV in inert solvents, or by a process in which
[C]dihydropyridinelactones of the general formula VI

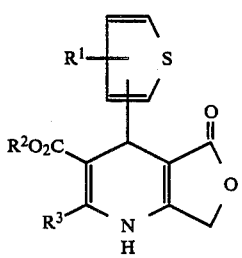 VI in which
R$^1$ and R$^3$ have the means given, are treated with bases in inert solvents and then alkylated with compounds of the general formula VII

R$^4$—X   VII in which
R$^4$ has the meaning given and
X represents halogen, preferably chlorine, bromine or iodine, or represents a diazo group, or represents a group of the formula —O—SO$_2$R$^5$, wherein
R$^5$ has the means of R$^4$ or represents phenyl, or tolyl.

The processes can be illustrated by the following equations, depending on the nature of the starting substances used:

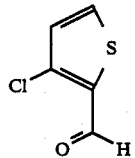

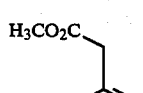 + 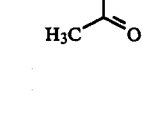 →

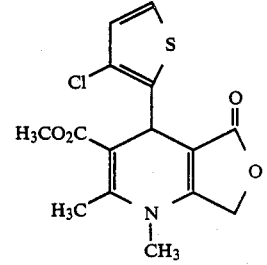

[B]

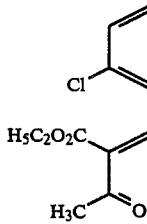 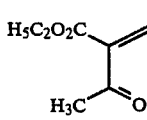 + 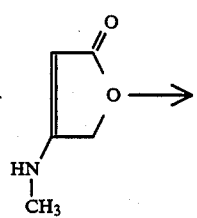 →

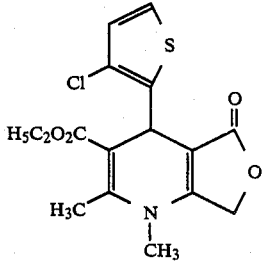

-continued

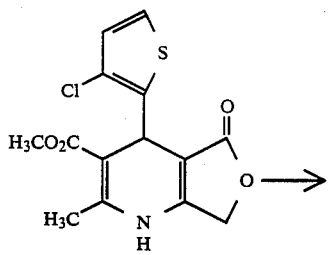

[C]

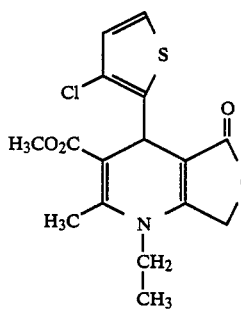

Possible solvents for processes A and B are all the organic solvents which do not change under the reaction conditions. These include, preferably, alcohols, such as methanol, ethanol, propanol or isopropanol, or ethers, such as diethyl ether, dioxane, tetrahydrofuran or glycol monomethyl or dimethyl ether, dimethylformamide, acetic acid, actonitrile, pyridine, dimethylsulphoxide or hexamethylphosphoric acid triamide. It is also possible to use mixtures of the solvents mentioned.

Possible solvents for process C are the customary inert organic solvents. These include, preferably, ethers, such as diethyl ether, dioxane or tetrahydrofuran, or acid amides, such as dimethylformamide or hexamethylphosphoric acid triamide, or dimethylsulphoxide or sulpholane, or hydrocarbons, such as benzene, xylene, toluene, hexane or petroleum fractions.

The bases customary for deprotonation can be used as the bases (process C). These include, preferably, alkali metal hydrides, such as sodium hydride or potassium hydride, or alkali metal amides, such as sodium amide, potassium diethylamide or lithium diisopropylamide, or alkali metal hydroxides, such as potassium hydroxide or sodium hydroxide, alkali metal alcoholates, such as potassium tert.-butanolate, potassium methylate or potassium ethylate, or metal-organyls, such as phenyllithium, n-butyllithium or tert.-butyllithium.

The reaction temperatures can be varied within a substantial range in processes A and B. The reaction is in general carried out in a range from +10° C. to +200° C., preferably from +20° C. to +150° C.

The reaction of the dihydropyridinelactone VI with the base (process C) is in general carried out in a temperature range from −80° C. to +200° C., preferably in a temperature range from −20° C. to +180° C. and particularly preferably from 20° C. up to the boiling point of the solvent used.

All the processes can be carried out under normal, increased or reduced pressure. They are in general carried out under normal pressure.

The aldehydes of the formula II used as starting substances are known or can be prepared by known methods (compare U.S. Pat. No. 2,601,479; U.S. Pat. No. 2,853,493; and J. prakt. Chem. 1964, 64).

The acetoacetic acid esters of the formula III used as starting substances are known or can be prepared by known methods (compare D. Borrmann, Houben-Weyl "Methoden der organischen Chemie" ("Methods of Organic chemistry") Volume VII 14, 230 et seq.)

The enamines of the formula IV used as starting substances are known or can be prepared by known methods (compared European Pat. No. 123,095).

The ylidene compounds of the formula V used as starting substances are known or can be prepared by known methods (compared G. Jones, "The Knoevenagel Condensation", Organic Reactions XV, 204 (1967)).

The dihydropyridinelactones of the formula VI used as starting substances are new in some cases. However, they can be prepared by known methods (DOS (German Published Specification) 3,205,399).

The compounds of the formula I according to the invention display a useful pharmacological action spectrum. With only a slight action on the circulation, they reduce the blood sugar and can thus be used for the treatment of diabetes.

The hypoglycaemic action of the substances to be investigated was tested on male Wistar rats weighing between 140 and 190 g. For this purpose, the rats were weighed 18 hours before administration of the substances and were divided into groups of 6 animals and fasted. The substances to be investigated were suspended in aqueous 0.75% strength tragacanth suspension using an Ultra-Turrax directly before the administration. The tragacanth suspension (control animals) or the substances suspended in tragacanth were administered by means of a stomach tube.

Blood was withdrawn from each rat from the retroorbital venous plexus 30, 60 and 120 minutes after the administration. Portions of 30 $\mu$l of blood were taken with an automatic diluter and deproteinated with 0.3 ml of uranyl acetate (0.16% strength). After the centrifugation, the glucose in the supernatant was determined photometrically on a Gemsaec Fast Analyzer by the glucose oxidase method with 4-amino-phenazone as the color reagent. The results were evaluated by the student t-test, $p<0.05$ being chosen as the significance limit.

Substances which effected a significant reduction of the blood glucose concentration in the rats of at least 10% at a point in time in comparison with the control group which received only tragacanth suspension were described as active.

The following Table 1 contains the changes found in the blood glucose concentrations in per cent of the control.

TABLE 1

| Substance (Patent Example No.) | Decrease in the blood glucose concentration in % of the control 10 mg/kg p.o. |
| --- | --- |
| 2 | 21 |
| 5 | 25 |
| 6 | 13 |

The present invention includes pharmaceutical formulations which contain, in addition to non-toxic, inert pharmaceutically suitable excipients, one or more active compounds according to the invention or which consist of one or more active compounds according to the invention, and processes for the preparation of these formulations.

The present invention also includes pharmaceutical formulations in dosage units. This means that the formulations are present in the form of individual parts, for example tablets, dragees, capsules, pills, suppositories and ampules, the active compound content of which correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half, one third or one quarter of a daily dose.

By non-toxic, inert pharmaceutically suitable excipients there are to be understood solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds in addition to the customary excipients, such as (a) fillers and extenders, for example starches, lactose, sucrose, glucose, mannitol and silicic acid, (b) binders, for example carboxymethylcellu, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) absorption accelerators, for example quaternary ammonium compounds (g) wetting agents, for example cetyl alcohol and glycerol monostearate, (h) adsorbents, for example kaolin and betonite, and (i) lubricants, for example talc, calcium stearate, magnesium stearate and solid polyethylene glycols, or mixtures of the substances listed under (a) to (i).

The tables, dragees, capsules, pills and granules can be provided with the customary coatings and shells, if appropriate containing opacifying agents, and can also be of such composition that they release the active compound or compounds only or preferentially in a certain part of the intestinal tract, if appropriate in a delayed manner, examples of embedding compositions which can be used being polymeric substances and waxes.

The active compound or compounds can also be in microencapsulated form, if appropriate with one or more of the abovementioned excipients.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, silicic acid, talc and zinc oxide, or mixtures of these substances.

Powders and sprays can contain, in addition to the active compound or compounds, the customary excipients, for example lactose, talc, silicic acid, aluminium hydroxide, calcium silicate and polyamide powder, or mixtures of these substances, and sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and additives which improve the smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the active compounds according to the invention.

The abovementioned pharmaceutical formulations are prepared in the customary manner by known methods, for example by mixing the active compound or compounds with the excipient or excipients.

The present invention also includes the use of the compounds of the formula I and/or salts thereof and of pharmaceutical formulations containing the compounds of the formula I and/or salts thereof in human and veterinary medicine for preventing, alleviating and/or healing the abovementioned diseases.

The active compounds or the pharmaceutical formulations can be administered orally, parenterally, intraperitoneally and/or rectally, preferably orally and parenterally.

In general, it has proved advantageous both in human and in veterinary medicine to administer the active compound or compounds according to the invention in total amounts of about 0.01 to about 200 mg/kg, preferably 0.1 to 50 mg/kg of body weight every 24 hours, if appropriate in the form of several individual administrations, to achieve the desired results.

However, it may be necessary to deviate from the dosages mentioned, and in particular to do so as a function of the nature and body weight of the subject to be treated, the nature and severity of the diseases, the nature of the formulation and of the administration of the medicament and the period or interval within which administration takes place. Thus it can in some cases suffice to manage with less than the abovementioned amount of active compound, while in other cases the abovementioned amount of active compound must be exceeded. The particular optimum dosage required and mode of administration of the active compounds can easily be specified by any expert on the basis of his expert knowledge.

PREPARATION EXAMPLES

EXAMPLE 1

Isopropyl 4-(3-chloro-2-thienyl)-2-methyl-5-oxo-1,4,5,7-tetrahydrofuro[3,4-b]-pyridine-3-carboxylate

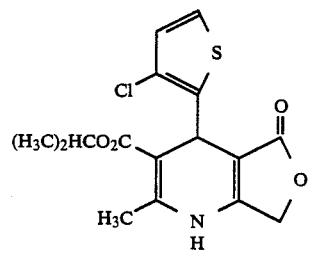

40 mmol of 3-chloro-thiophene-2-carbaldehyde, 40 mmol of 3-acetoxyacetoacetic acid ester and 40 mmol of isopropyl 3-aminocrotonate are boiled under reflux over NaOH in EtOH, alcoholic hydrochloric acid is then added and the mixture is boiled for 1 hour. It is concentrated and the residue is crystallized.

Yield: 50% of theory.
Melting point: 194°-5° C.

EXAMPLE 2

Isopropyl 4-(3-chloro-2-thienyl)-1-ethyl-2-methyl-5-oxo-1,4,5,7-tetrahydrofuro[3,4-b]pyridine-3-carboxylate

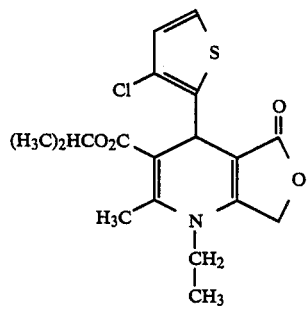

10 mmol of isopropyl 4-(3-chloro-2-thienyl)-2-methyl-5-oxo-1,4,5,7-tetrahydrofuro[3,4b]pyridine-3-carboxylate are dissolved in 25 ml of dimethylformamide and deprotonated with NaH, and 20 mmol of ethyl iodide are added. After the mixture has been stirred at room temperature for 1 hour, it is concentrated, water is added to the residue and the product is filtered off with suction and recrystallized from methanol.

Yield: 75% of theory.
Melting point: 76°-80° C.

The following compounds were prepared analogously to Example 1:

EXAMPLE 3

Isopropyl 4-(2-chloro-3-thienyl)-2-methyl-5-oxo-1,4,5,7-tetrahydrofuro[3,4-b]pyridine-3-carboxylate

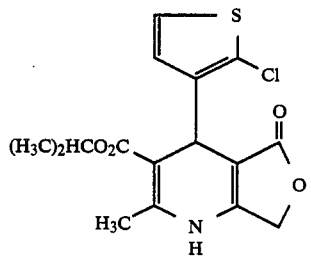

Yield: 40% of theory.
Melting point: 200°-202° C.

EXAMPLE 4

Isopropyl 2-methyl-4-(3-methyl-2-thienyl)-5-oxo-1,4,5,7-tetrahydrofuro[3,4-b]pyridine-3-carboxylate

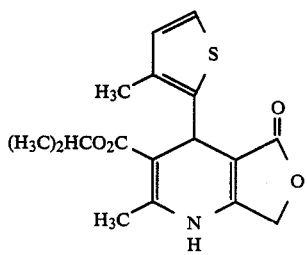

Yield: 15% of theory.
Melting point: 207°-8° C.

The following compounds were prepared analogously to Example 2:

EXAMPLE 5

Isopropyl 4-(2-chloro-3-thienyl)-1-ethyl-2-methyl-5-oxy-1,4,5,7-tetrahydrofuro[3,4-b]pyridine-3-carboxylate

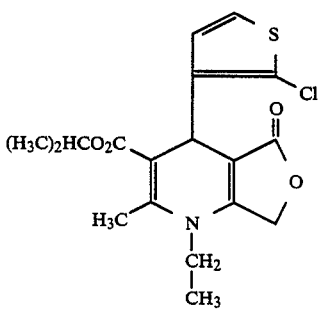

Yield: 45% of theory.
Melting point: 140°-5° C.

EXAMPLE 6

Isopropyl 1-ethyl-2-methyl-4-(3-methyl-2-thienyl)-5-oxo-1,4,5,7-tetrahydrofuro[3,4-b]pyridine-3-carboxylate

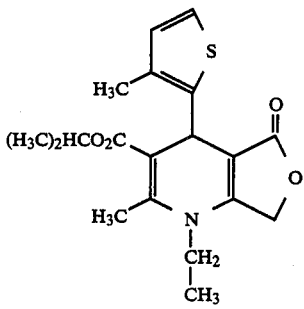

Yield: 40% of theory.
Melting point: 88°–93° C.

EXAMPLE 7

Isopropyl 1,2-dimethyl-4-(3-methyl-2-thienyl)-5-oxo-1,4,5,7-tetrahydrofuro[3,4-b]pyridine-3-carboxylate

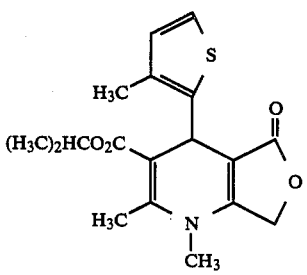

Yield: 60% of theory.
Melting point: 170°–4° C.

It is understood that the specification and examples are illustrative but not limitative of the present invention and that other embodiments within the spirit and scope of the invention will suggest themselves to those skilled in the art.

We claim:

1. A 4-thienyl-dihydropyridine of the formula

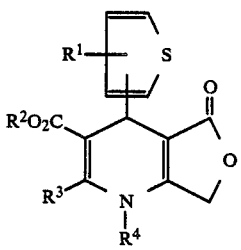

in which
$R^1$ represents fluorine or chlorine, or represents straight-chain or branched alkyl with up to 4 carbon atoms,
$R^2$ represents a straight-chain, branched or cyclic hydrocarbon radical which has up to 8 carbon atoms, is optionally interrupted by an oxygen atom and is optionally substituted by one or more fluorine, chlorine, phenyl, hydroxyl, cyano, amino, $C_1$-$C_3$-alkylamino, di-$C_1$-$C_3$-alkylamino or N-benzyl-N-methyl-amino groups,
$R^3$ represents $C_1$-$C_4$-alkyl which is optionally substituted by hydroxyl and
$R^4$ represents ethyl,
or a physiologically acceptable salt thereof.

2. A compound wherein such compound is isopropyl 4-(3-chloro-2-thienyl)-1-ethyl-2-methyl-5-oxo-1,4,5,7-tetrahydrofuro[3,4-b]pyridine-3-carboxylate of the formula

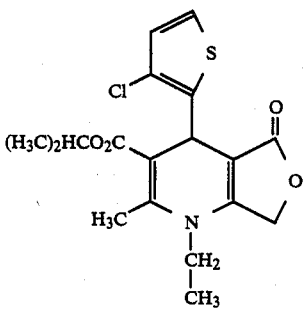

or a physiologically acceptable salt thereof.

3. A compound wherein such compound is isopropyl 4-(2-chloro-3-thienyl)-1-ethyl-2-methyl-5-oxo-1,4,5,7-tetrahydrofuro[3,4-b]pyridine-3-carboxylate of the formula

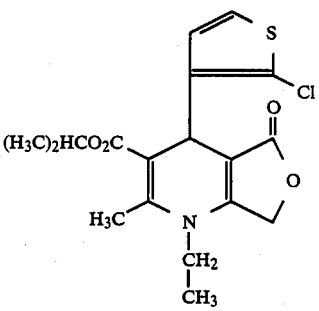

or a physiologically acceptable salt thereof.

4. A compound wherein such compound is isopropyl 1-ethyl-2-methyl-4-(3-methyl-2-thienyl)-5-oxo-1,4,5,7-tetrahydrofuro[3,4-b]pyridine-3-carboxylate of the formula

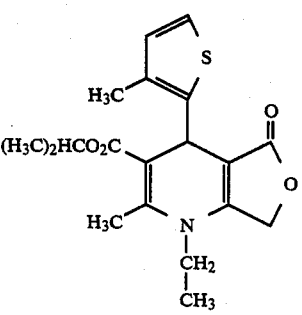

or a physiologically acceptable salt thereof

* * * * *

UNITED STATES PATENT AND TRADEMARK OFFICE
CERTIFICATE OF CORRECTION

PATENT NO. : 4,801,715
DATED : Jan. 31, 1989
INVENTOR(S) : Goldmann et al.

It is certified that error appears in the above-identified patent and that said Letters Patent is hereby corrected as shown below:

| | |
|---|---|
| Title Page, under "Abstract", line 13 after formula | Delete "N-benzyl" in second instance |
| Col. 1, line 32 | Insert -- - -- after "C$_6$" in second instance |
| Col. 1, line 48 | Insert -- - -- after "C$_6$" |
| Col. 2, line 12 | Insert --isomers,-- after "their" |
| Col. 6, line 11 | Delete "compared" and substitute --compare-- |
| Col. 10, line 49 | Correct spelling of --oxo-- |

Signed and Sealed this

Second Day of January, 1990

Attest:

JEFFREY M. SAMUELS

Attesting Officer    Acting Commissioner of Patents and Trademarks